United States Patent [19]

Gainer

[11] 4,176,179

[45] Nov. 27, 1979

[54] METHOD FOR TREATING ARTHRITIS

[75] Inventor: John L. Gainer, Charlottesville, Va.

[73] Assignee: The University of Virginia Alumni Patents Foundation, Charlottesville, Va.

[21] Appl. No.: 897,002

[22] Filed: Apr. 17, 1978

[51] Int. Cl.² .................... A61K 31/13; A61K 31/19; A61K 31/23; A61K 31/70

[52] U.S. Cl. .................................. 424/180; 424/312; 424/317; 424/318; 424/325; 424/343

[58] Field of Search ............... 424/313, 317, 180, 312, 424/318, 325, 343

[56] References Cited

U.S. PATENT DOCUMENTS 4,070,460    1/1978    Gainer .................. 424/180

OTHER PUBLICATIONS

Chem. Abst., 81-45530m, (1974).
Chem. Abst., 83-90815k, (1975).

Primary Examiner—Stanley J. Friedman
Attorney, Agent, or Firm—Oblon, Fisher, Spivak, McClelland & Maier

[57] ABSTRACT

Arthritis in mammals is treated by administering to said mammal an effective dose of a water soluble carotenoid.

4 Claims, 2 Drawing Figures

METHOD FOR TREATING ARTHRITIS

BACKGROUND OF THE INVENTION

1. Field of the Invention

This invention relates to a novel technique for treating arthritis in mammals.

2. Description of the Prior Art

In Applicant's prior applications, now U.S. Pat. Nos. 3,853,993 and 3,788,468, Applicant disclosed that certain water-soluble carotenoids had been observed to possess quite unique properties. In particular, these water-soluble carotenoids have been found to increase the diffusivity of oxygen through aqueous media. Applicant theorized that this phenomenon might be applied to effect desirable biological effects. In particular, Applicant theorized that if oxygen diffusivity in aqueous media could be enhanced, that this effect could be applied to increase the diffusivity of oxygen in blood. Applicant theorized further that by increasing the diffusivity of oxygen in the blood, atherosclerosis, which has long been theorized to be a disease resulting from local hypoxia of the vascular walls, could be successfully treated. This theory was applied to certain test animals, and, to the satisfaction of the inventors, the theory was proven to be correct, and in fact, a seemingly successful treatment of atherosclerosis was obtained.

Applicant has now continued to study the biological properties of this most unusual class of compounds, with the result that a new biological property has been discovered which is the subject matter of this application.

SUMMARY OF THE INVENTION

It has been found that the water-soluble carotenoid compounds, such as crocetin and crocin, can be used effectively for the treatment of arthritis in mammals.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
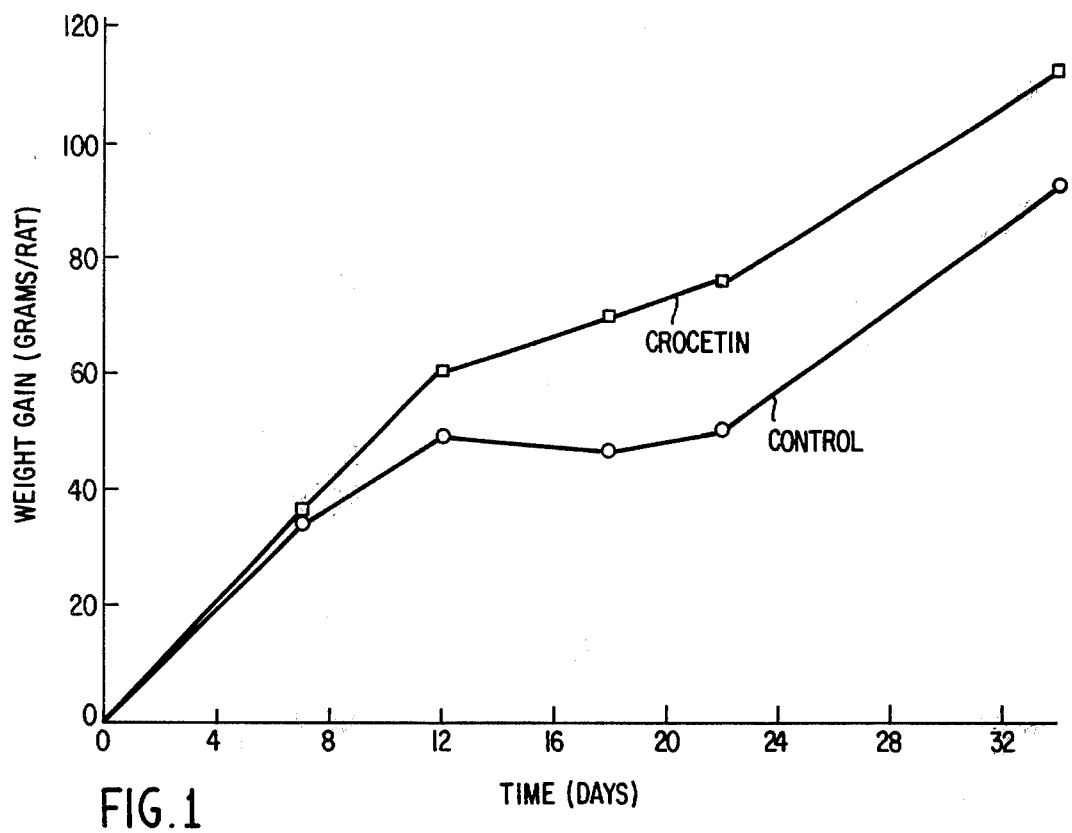
FIG. 1 shows the weight gain of the treated and untreated rats in the study of Example 1.

Rhuematoid arthritis is a chronic syndrome characterized by a non-specific inflammation of the peripheral joints, usually symmetrical with reference to affected joints as well as to the right and left sides of the body. It results in progressive destruction of articular and priarticular structures. The etiology is unknown. About 1% of all populations are affected, women two to three times more commonly than men.

Onset may be abrupt, with simultaneous inflammation in multiple joints, or insidious, with progressive involvement of new joints. Tenderness can be elicited in nearly all "active" joints and is the most sensitive physical sign. Synovial thickening, the most specific physical finding, is eventually seen in many, but not often in all, active joints. Deformities may develop rapidly. Currently-used drugs for treatment include: salicylates, gold compounds, phenylbutazone, hydroxychloroquine, indomethacin and corticosteroids. These latter compounds remain the most effective of these so-called "anti-inflammatory" drugs. However, since it has been reported that steroid compounds result in undesirable side-effects, it is quite desirable to have a new drug for the treatment of this ailment, which strikes many, especially older, people.

The carotenoids useful in the treatment of arthritis are those of the form:

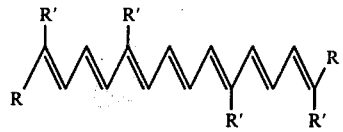

wherein each R may represent a hydrophilic group and each R' represents hydrogen or methyl. Suitable hydrophilic groups include the carboxyl groups or the ester groups of the form COOR" wherein R" represents a soluble sugar group, such as $C_{12}H_{21}O_{10}$, an alkanol group, such as $-CH_2-OH$, $-CH_2-CH_2-OH$, or $-CH_2-CH_2-CH_2-OH$, or a carboxy substituted lower alkyl, such as $-CH_2-COOH$, $-CH_2-CH_2COOH$ or $-CH_2-CH_2-CH_2COOH$, or each R and R" may represent a lower alkanol group, such as $-CH_2-OH$, $-CH_2-CH_2-OH$, or $-CH_2-CH_2-CH_2-OH$, a hydroxy group, or an amine group of the form $-NH$ or $NR'''$ wherein $R'''$ is a lower alkyl, lower alkanol or carboxy substituted lower alkyl, or a hydroxy substituted lower alkyl, such as $-CH_2-CH_2-OH$, $-CH_2-OH$, or $-CH_2-CH_2-CH_2-OH$.

Most preferred are crocetin, also known as 8,8'-diapo-8,8'-carotenedioic acid, or crocin, also known as digentiobiosyl 8,8'-diapo-8,8'-carotenedioate.

For the treatment of rheumatoid arthritis the water soluble carotenoids can be administered to the mammal either orally in the form of a capsule or tablet, or intravenously or intramuscularly. The effective dosage of the crocetin, of course, will probably depend upon the severity of the condition, the stage and the individual characteristics of each mammal being treated. It is expected, however, that the water soluble carotenoids, and particularly crocetin or crocin, may be administered in a dosage ranging from about 0.005 mg active ingredient per kg of body weight per week to 100 mg and preferably from 0.01 to 10 mg per kg of body weight per week.

In order to test the effectiveness of a drug against arthritis, it is necessary to use an animal model. There does not seem to be an animal model which completely replicates rheumatoid arthritis in humans; however, the use of adjuvant and Mycobacterium induced arthritis provides a model of chronic joint inflammation, and is a frequently-used animal model for arthritis. The most commonly used experimental animals are rats, and they were used in this study. The arthritis was developed by an intradermal injection of *Mycobacterium butyricum* (Difco Laboratories, Detroit, Mich.) suspended in mineral oil. These injections were made in the right hind foot of the rats, and the arthritis first developed in that foot. However, secondary lesions in other joints also appeared later; in the other hind foot, the front feet, the tail and the ears. This model fits the conditions for a chronic inflammation of the joints, and shows all those symptoms which are: swelling, redness, heat, pain, synovial proliferation, abnormal connective tissue formation and cellular infiltration into the joint space. Thus, in many aspects the disease characteristics of these rats are similar to those of rheumatoid arthritis in humans.

Although the carotenoids have been identified herein as "water soluble carotenoids", it should be understood that they are also soluble in hydrocarbons due to their long chain hydrocarbon structure.

Having generally described the invention, a more complete understanding can be obtained by reference to certain specific examples, which are included for purposes of illustration only and are not intended to be limiting unless otherwise specified.

EXAMPLES

Example 1

In order to investigate the effect of crocetin on arthritis, the following experiment was performed on 10 male Sprague-Dawley rats.

These rats weighed about 150 grams each at the beginning of the experiment, and were housed at the University of Virginia Vivarium. They were fed pelleted rat chow and water ad libitum.

The rats were all injected with 0.05 ml of mineral oil containing 0.5 mg of *Mycobacterium butyricum*. The injections were performed intradermally in the right hind paw. Half of the rats were used as a control group. The other half were given daily injections of sodium crocetin, starting at the same time as the injections of *Mycobacterium butyricum*. The crocetin injected was at a level of 1.0 mg/kg of sodium crocetin. The injected solution also contained sodium carbonate, and these were all dissolved in distilled water and injected intraperitoneally.

The progress of the arthritis was followed using 4 criteria:

1. Weight gain: Arthritic rats gain less weight.
2. Paw thickness: The paw injected with *Mycobacterium butyricum* will swell more with severe arthritis.
3. Lysozyme levels: The level of this enzyme increases with the severity of the arthritis.
4. Secondary lesions: The appearance of arthritic disease in the ears, tail and other limbs of the rats.

Figure 2:
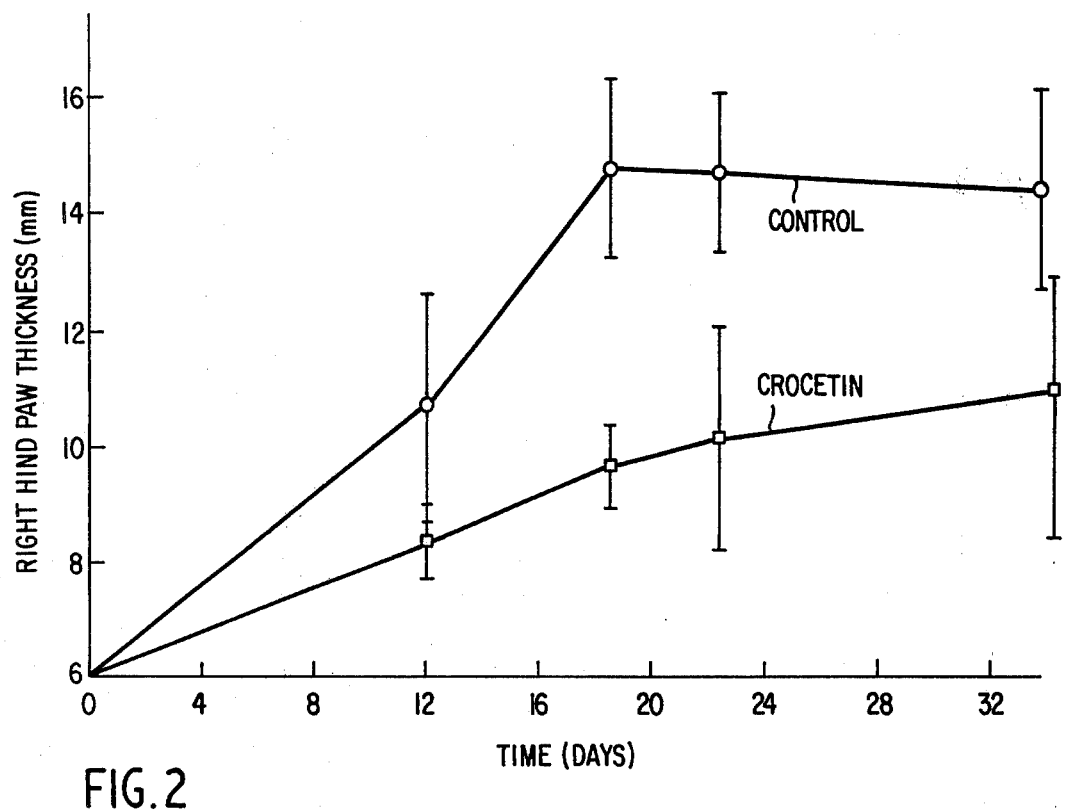
FIG. 2 shows the thickness of the arthritic paws of the treated and untreated rats in the study of Example 1.

Using all criteria, the crocetin greatly lessened the severity of the arthritis. The treated rats gained more weight (see FIG. 1), showed less swelling of the affected paws (see FIG. 2), and had less lysozyme in their blood plasma, as is shown in Table 1.

TABLE 1

| Lysozyme Levels of Arthritic Rats | |
|---|---|
| Group | Lysozyme Activity (units per ml plasma±S.D.) |
| Control | 187 ± 30 |
| Crocetin-treated | 132 ± 24* |

*P < .01 that averages are the same.

The control rats also showed severe secondary lesions in the ears, tail, other hind paw and front paws. The crocetin-treated group showed virtually no secondary lesions. Thus, using these four criteria, the crocetin appears to be effective in treating arthritis.

Having now fully described the invention, it will be apparent to one of ordinary skill in the art that many changes and modifications can be made without departing from the spirit or scope of the invention as set forth herein.

What is claimed as new and intended to be covered by Letters Patent is:

1. A method for treatment of rheumatoid arthritis in a mammal which comprises administering to said mammal in need of treatment an effective dose sufficient to alleviate the symptoms of rheumatoid arthritis, of a water soluble carotenoid having the formula

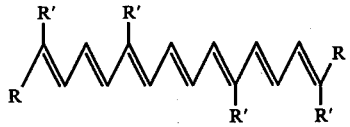

wherein each R is a hydrophilic group, and wherein each R' is hydrogen or methyl.

2. The method of claim 1, wherein said water-soluble carotenoid is crocin.

3. The method of claim 1, wherein said water-soluble carotenoid is crocetin.

4. The method of claim 1, wherein said water-soluble carotenoid is administered intravenously or orally at a dose rate of from 0.001 mg to 1000 mg active ingredient per kg of body weight per week.

* * * * *